United States Patent [19]

Kalnajs et al.

[11] Patent Number: 5,880,772
[45] Date of Patent: *Mar. 9, 1999

[54] MACHINE VISION IMAGE DATA ACQUISITION SYSTEM

[75] Inventors: Andrejs K. Kalnajs, Madison; Robert G. Burt, Huntsville, both of Ala.

[73] Assignee: DaimlerChrysler Corporation, Auburn, Mich.

[ * ] Notice: This patent issued on a continued prosecution application filed under 37 CFR 1.53(d), and is subject to the twenty year patent term provisions of 35 U.S.C. 154(a)(2).

[21] Appl. No.: 969,717

[22] Filed: Mar. 17, 1997

Related U.S. Application Data

[63] Continuation of Ser. No. 321,648, Oct. 11, 1994, abandoned.

[51] Int. Cl.⁶ .................................................. H04N 7/18
[52] U.S. Cl. ............................................. 348/87; 348/126
[58] Field of Search ................................ 348/87, 126, 92, 348/94, 95, 86, 131, 132, 125; 382/151, 150, 149, 148, 147, 146, 145

[56] References Cited

U.S. PATENT DOCUMENTS

| | | | |
|---|---|---|---|
| 2,434,385 | 1/1948 | Bonnet | 88/16.6 |
| 3,895,867 | 7/1975 | Lo et al. | 355/77 |
| 4,379,308 | 4/1983 | Kosmowski et al. | 348/126 |
| 4,677,473 | 6/1987 | Okamoto et al. | 348/131 |
| 4,799,175 | 1/1989 | Sano et al. | 382/151 |
| 4,851,698 | 7/1989 | Hippenmeyer | 250/578 |
| 4,872,052 | 10/1989 | Liudzius et al. | 358/106 |
| 4,978,220 | 12/1990 | Abramovich et al. | 356/394 |
| 5,008,743 | 4/1991 | Katzir et al. | 358/101 |
| 5,030,008 | 7/1991 | Scott et al. | 356/394 |
| 5,050,111 | 9/1991 | Ayata et al. | 364/559 |
| 5,051,825 | 9/1991 | Cochran et al. | 358/106 |
| 5,121,438 | 6/1992 | Kawauchi et al. | 382/8 |
| 5,140,643 | 8/1992 | Izumi et al. | 348/87 |
| 5,144,681 | 9/1992 | Kitakado et al. | 382/894 |
| 5,245,411 | 9/1993 | Dury | 356/446 |
| 5,245,421 | 9/1993 | Robertson et al. | 358/101 |
| 5,249,035 | 9/1993 | Yamanaka | 356/376 |
| 5,333,208 | 7/1994 | Massen | 348/92 |
| 5,377,279 | 12/1994 | Hanafusa et al. | 348/133 |
| 5,440,648 | 8/1995 | Roberts et al. | 348/133 |
| 5,477,268 | 12/1995 | Shimbara et al. | 348/128 |

*Primary Examiner*—Bryan Tung

[57] ABSTRACT

An image data acquisition system for acquiring visible spectrum image data used in the inspection of circuit boards. The system comprises a rigid structure having upper and lower banks of cameras and telecentric lenses mounted in axial pairs at a substantially right angle to the circuit boards which are transported on the conveyor below. The cameras have overlapping fields of view which form a directionally contiguous band or two-dimensional web of sensor coverage. A beam splitter and mirror arrangement is mounted to the structure under the upper and lower banks such that light striking the mirror is reflected into the lower bank of cameras while light striking the beam splitter is partially reflected toward the mirror and partially transmitted through the body of the beam splitter into the upper bank of cameras.

14 Claims, 6 Drawing Sheets

MACHINE VISION IMAGE DATA ACQUISITION SYSTEM

This application is a continuation of application Ser. No. 08/321,648, filed Oct. 11, 1994 abandoned.

FIELD OF INVENTION

The present invention relates to a machine vision image data acquisition system for acquiring visual image data of electronic circuits boards. More particularly, the present invention relates to a novel method and apparatus for acquiring visual image data for use in a machine vision inspection system that detects errors in the placement of discrete through-hole technology components inserted through printed circuit boards, solder paste screened onto bare circuit boards, and/or surface mounted device (SMD) technology components mounted on printed circuit boards.

BACKGROUND OF THE INVENTION

The acquisition of visual-spectrum image data for machine vision inspection of printed circuit boards conventionally has been performed by "moving camera" systems which employ typically a single video camera mounted on a movable staging structure. Such systems are programmed to step the video camera over the circuit board progressively in a serpentine fashion along an x-y coordinate system. The moving camera is stopped and snapped synchronously with strobe light flashes to acquire overlapping images of the entire circuit board at predetermined points along the serpentine coordinate path.

Unfortunately, single moving camera systems prove disadvantageous in the high-volume production of small electronic circuit boards such as those used for automotive engine, message display, transmission and brake controllers due to the unacceptably long cycle times that result from having to continuously move and stop the video camera over the printed circuit board.

Designers of machine vision image data acquisition systems have attempted to reduce the long cycle times of moving camera systems by mounting multiple cameras on a fixed staging structure. Early multiple fixed-camera systems, such as those manufactured by IRI (International Robamation Intelligence) of Carlsbad, Calif., mounted video cameras in four horizontally opposing banks on a large fixed staging structure that required a heavy frame for support. The heavy frame occupied a large footprint on the manufacturing facility floor which contributed to the expense of these systems. The video camera lenses employed had long object distances (approximately 22") and were directed at mirror assemblies oriented 45 degrees to both the cameras and the printed circuit boards. The printed circuit boards were advanced synchronously on the conveyor under the mirror assemblies with snaps of the video cameras. This mirror design disadvantageously inverted the images of the area of interest acquired on the printed circuit board requiring image processing programs to mathematically flip the image back to its actual orientation in space. In addition, the opposing camera and lens configuration made alignment and calibration of the video cameras complex.

Although an increase in cycle time and throughput was achieved in early multiple fixed camera designs, the system resolution was limited to camera arrays having at least 2 mil pixels (0.002 inches per pixel) due to the mounting constraints of the video cameras which had relatively large body sizes. In addition, lenses with long object distances were required to minimize distortion and perspective errors. Complex software, if available, was required to improve inspection performance.

Thus, image data acquisition systems employing multiple fixed cameras with large body or housing dimensions mounted horizontally relative to the conveyor have proven impractical in applications involving relatively small printed circuit boards that are densely populated with small SMD components. Such applications require high system resolution (1 mil per pixel), fast cycle times, and a small system footprint to fit into existing automated manufacturing lines.

Therefore, to reduce cycle time and increase throughput, and to improve data image acquisition quality, a multiple camera image data acquisition system is desired with higher system resolution and cycle times but small physical packaging dimensions.

SUMMARY OF THE INVENTION

An image data acquisition system is described for acquiring visible spectrum image data used in the inspection of printed circuit boards. The system comprises a rigid structure that straddles a conveyor transporting circuit boards. The structure has two camera mounting surfaces located at upper and lower elevations of the structure with a plurality of cameras mounted on these surfaces forming upper and lower camera banks. The cameras have overlapping fields of view which form a directionally contiguous band or two-dimensional web of sensor coverage. Also mounted on the structure in axial pairs with the cameras are a plurality of telecentric lenses oriented such that each of the camera and lens axes is oriented at a substantially right angle to the circuit board under inspection. A beam splitter and a mirror are attached to the structure under the upper and lower banks such that light striking the mirror is reflected into the lower bank while light striking the beam splitter is partially reflected toward the mirror and partially transmitted through the body of the beam splitter into the upper bank. Finally, a light source which delivers evenly distributed illumination to the surface of the printed circuit board is mounted to the structure.

DETAILED DESCRIPTION OF THE PREFERRED EMBODIMENT

Figure 1:
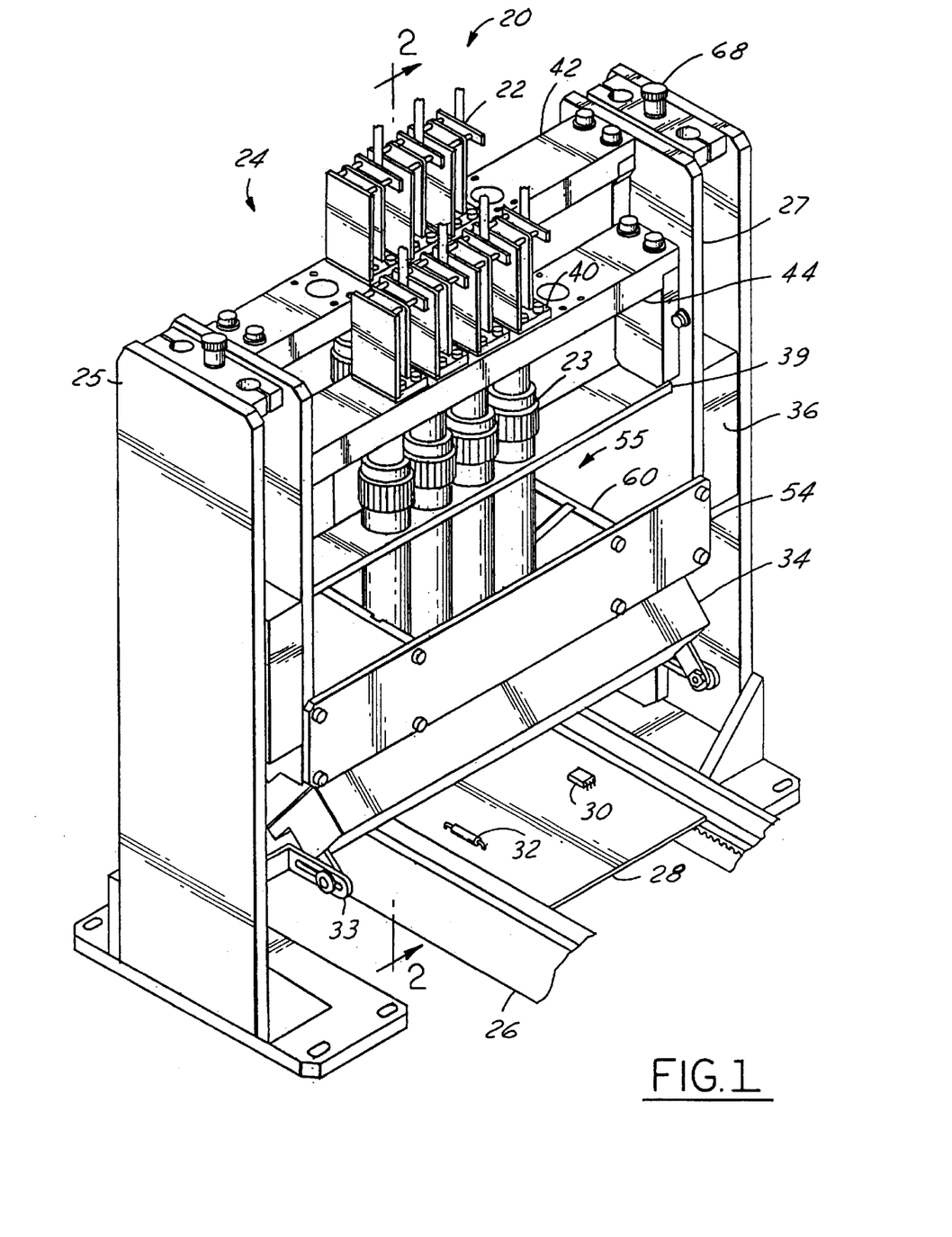
FIG. 1 is a perspective view of the machine vision image data acquisition system configured with 1 mil resolution lenses inspecting a printed circuit board on a conveyor unit.

Referring now to the drawings wherein like components among the several views are indicated by the same numeral, FIG. 1 depicts the machine vision image data acquisition system 20 with two banks of L-bracket video cameras 22 and lenses 23 mounted at parallel levels on an adjustable multicamera staging structure 24 that straddles an automated conveyor unit 26. Printed circuit boards 28 screened with solder paste or populated with surface-mounted devices (SMDs) 30 and/or discrete through-hole technology components 32 are transported by the automated conveyor unit 26 under the staging structure 24 where they are evenly illuminated during inspection by two light delivery bars 34 with adjustable brackets 33 mounted on the inside vertical stage supports 27 of the staging structure 24.

The light delivery bars 34 deliver intense and uniform illumination to the printed circuit boards 28 enabling the L-bracket video cameras 22 to capture clear visible spectrum images of predetermined areas of interest on the printed circuit board(s) 28. The light delivery bars 34 also provide illumination to the precision photo-tool 64 shown in FIG. 7a for the alignment and calibration of the L-bracket video cameras 22 and lens 23 described below in step 106 of FIG. 8. The light delivery bars 34 used in the preferred embodiment are part of a distributed light delivery system described in U.S. patent application Ser. No. 08/222,757 filed Apr. 4, 1994.

Referring again to FIG. 1, an adjustable slide assembly 36 is bolted between each of the two outside vertical frame supports 25 and the adjacent inside vertical stage supports 27. The slide assemblies 36 are used to raise and lower the staging structure 24 above the conveyor unit 26 during the conveyor unit alignment process described below in reference to FIG. 8. The slide units 36 used in the preferred embodiment are both Stelron Slide Model #ES7-12-C-LS, each having 5.25"×6.25" mounting plates with 12" shafts and lead screws.

Figure 2:
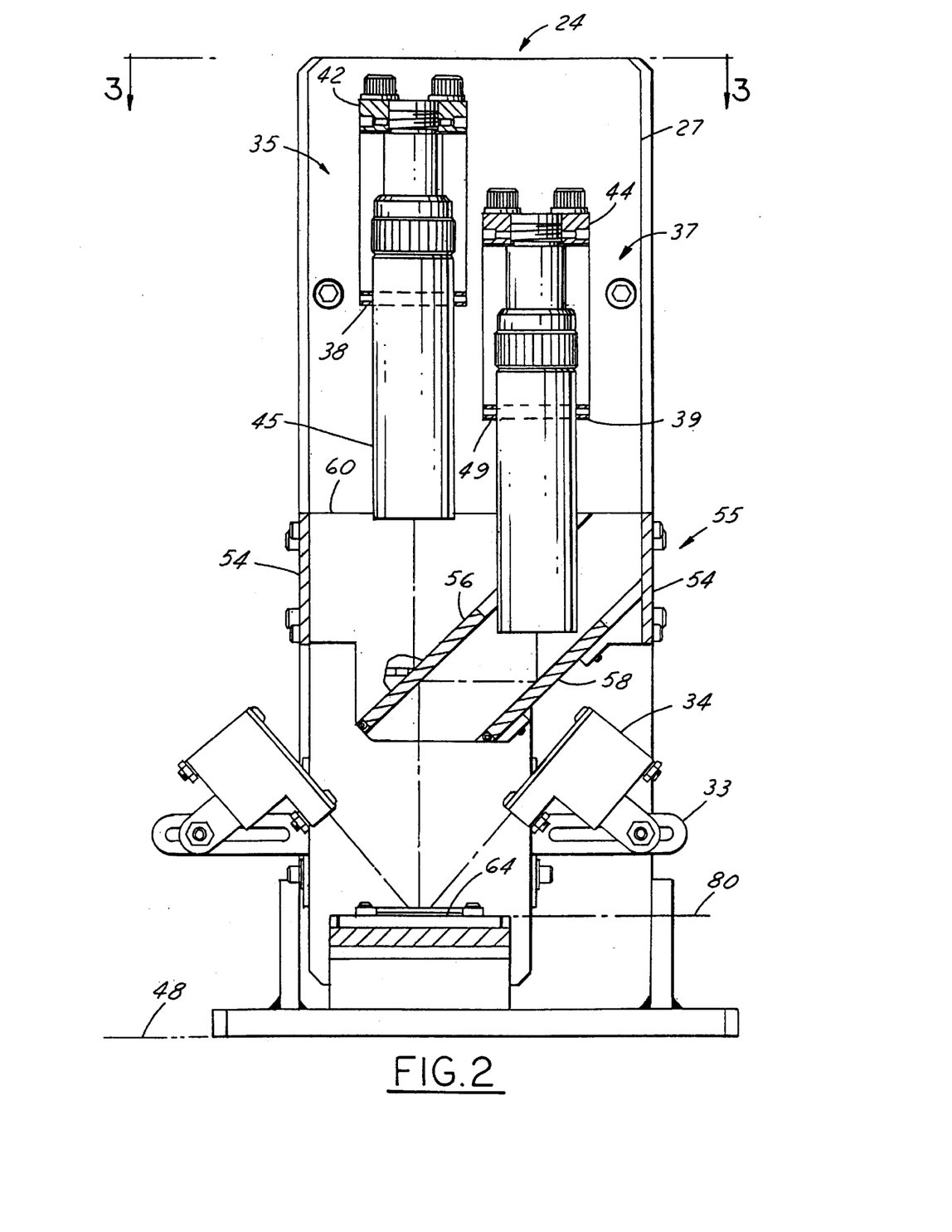
FIG. 2 is a vertical cross-sectional view taken along line 2—2 of FIG. 1 showing the multicamera staging structure configured with a photo-tool fixture assembly.

Referring now to FIG. 2, the lenses 23 and L-bracket video cameras 22 are arranged in axially mounted pairs on the mounting bars 42 and 44 in the upper and lower camera banks 35 and 37, respectively, on the multicamera staging structure 24. The L-bracket video cameras 22 are mounted on top of the mounting bars 42 and 44 with camera mounting screws 40 while the lenses 23 screw from below into threaded holes in the mounting bars 42 and 44. The barrels 45 of the lenses 23 are retained in the upper and lower alignment plates 38 and 39, respectively, with locking set screws 49. The camera mounting screws 40 and locking set screws 49 are used to align and calibrate the L-bracket video cameras 22 and the lenses 23, respectively, to the top surface of the precision photo-tool 64, which defines the calibration plane 80, during the camera and lens calibration process. The alignment plates 38 and 39 and the mounting bars 42 and 44 are mounted on the inside vertical stage supports 27 parallel to the mounting surface of multicamera staging structure 48. Thus, the slide assemblies 36 provide a convenient way to raise and lower the multicamera staging structure 24 as a unit above the mounting surface of the multicamera staging structure without disturbing either the pcb inspection plane 41 on the conveyor unit 26 or the camera and lens calibration plane 80 once parallelism between these two planes has been established in the conveyor alignment process described below in conjunction with FIG. 8.

The lenses 23 used in the preferred embodiment are high resolution telecentric lenses purchased from Melles Groit Optics of Rochester, N.Y. These lenses 23 each have a 1.5 inch diameter barrel and a ⅔ Charge Coupled Device (CCD) camera-array format with a 754×580 pixel camera array for a pixel resolution of 1 mil. The lenses 23 were designed for Chrysler Corporation to have a predetermined telecentricity of less than 1%, distortion of less than 0.05%, magnification of 0.379×±5% and a short nominal object distance of 7.53 inches. The magnification tolerance allows each lens 23 to be focused independently to the calibration plane 80. The telecentric lenses 23 used in the preferred embodiment eliminate distortion errors at the edge of the cameras' 22 field of view and accurately gauge three dimensional features within the field of view to provide constant x/y plane measurement within the depth of field without having to compensate for the large perspective variations common with conventional lenses. Any remaining field of view variation resulting from manufacturing tolerances or any alignment offsets between the video cameras 22 and the lenses 23 remaining after camera and lens calibration has been performed can be compensated for by the image processing software that receives the output data from the machine vision image data acquisition system 20. The large diameter of the lenses 23 enables them to collect more light thereby increasing the sensitivity of the machine vision image data acquisition system 20. In addition, the short object distance and barrel length of the lenses 23 allows the machine vision image data acquisition system 20 to be packaged as a compact tabletop unit.

Figure 4:
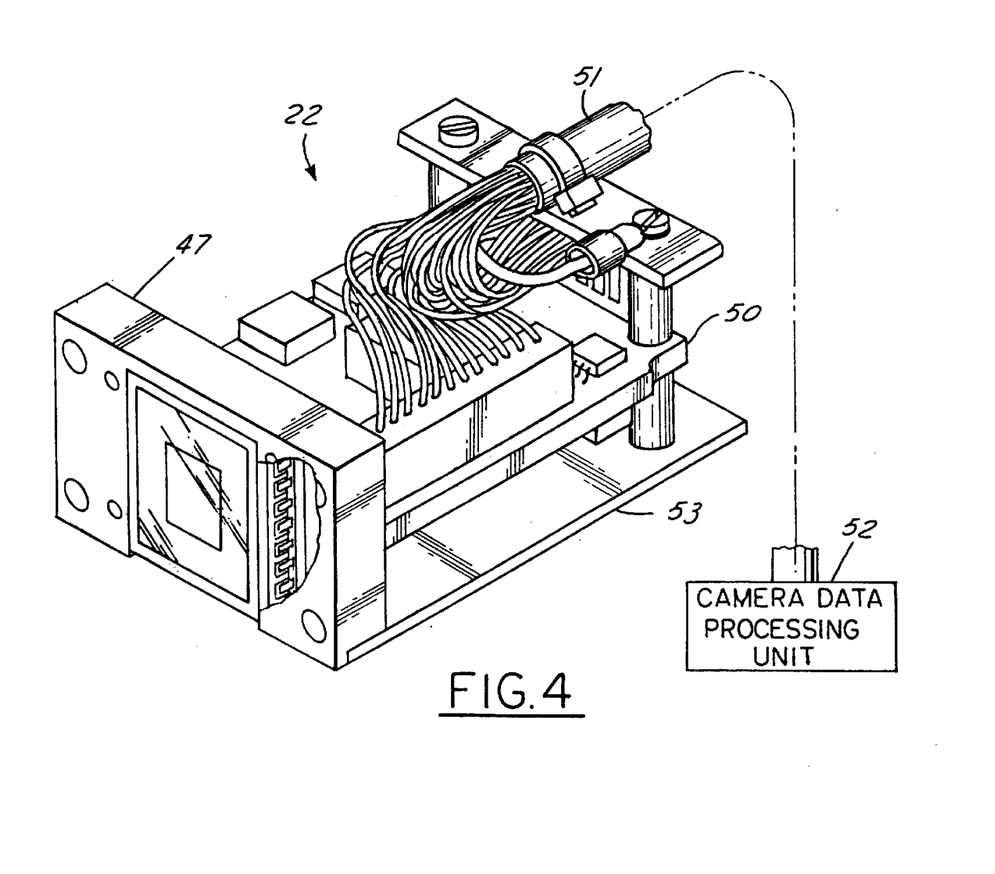
FIG. 4 is a perspective view of a L-bracket video camera.

Referring now to FIG. 4, the L-bracket video cameras 22 used in the preferred embodiment were manufactured for Chrysler Corporation by CIDTEC of Liverpool, N.Y. These cameras 22 have a narrow L-bracket design that allows them to be mounted in close proximity to one another on the camera mounting bars 42 and 44, a design which allows the machine vision image data acquisition system 20 to acquire high resolution images. A mask change was made to the firmware contained in the 754×580 CID array 46 of the L-bracket video cameras 22 to adapt the CID array 46 to scan progressively. The CID array 46 senses light input which has been transmitted through the lens 23. A pcb sampling and conditioning circuit 50 samples the output signal present on the pins of the CID array 46 then amplifies and conditions this signal for transmission via a six foot camera cable 51 to an image data processing unit 52 located remotely from the L-bracket video camera 22. An electrical noise isolation shield (not shown in the drawings) is mounted between the upper and lower banks 35 and 37 to reduce cross-talk among the pcb sampling and conditioning circuit boards 50 mounted on each bank 35 or 37. The side shield 53 which forms part of each L-bracket video camera 22 reduces cross-talk between L-bracket video cameras 22 mounted on the same bank 35 or 37.

Referring again to FIGS. 1 and 2, a beam splitter/mirror assembly 55 is mounted on optics mounting plates 54 between the inside vertical stage supports 27 of the staging structure 24 under the two camera banks 35 and 37. Two optics end plates 60 are mounted between the two optics mounting plates 54. The beam splitter 56 and the mirror 58 are retained by optics end plates 60 at an angle of 45 degrees with respect to the common axes of the L-bracket video cameras 22 and the lenses 23. The beam splitter 56 has an anti-reflective coating which provides a 50% transmission and 50% reflection ratio for light rays incident on its surface. The mirror 58 is a first surface mirror which reflects 94% of the light rays incident on its first mirror surface.

As shown in FIG. 2, the mounting plates 54 locate the beam splitter 56 under the upper bank 35 and the mirror 58 under the lower bank 37 of lenses 23. Light rays emanating from an area of interest on the photo-tool 64 or from the printed circuit board 28 are partially transmitted through the glass body of the beam splitter 56 into the upper bank 35 of cameras 22 while the remaining light rays are reflected onto the mirror 58. The mirror 58 directs, or reflects for a second time, light rays incident on its surface into the lower bank 37 of cameras 22. In either case, the optical path, or distance traveled by the light rays, as measured from the calibration plane 80 to the lens 22 in either bank 35 or 37 is identical. In the preferred embodiment the optical path is nominally 7.53 inches.

Figure 7A:
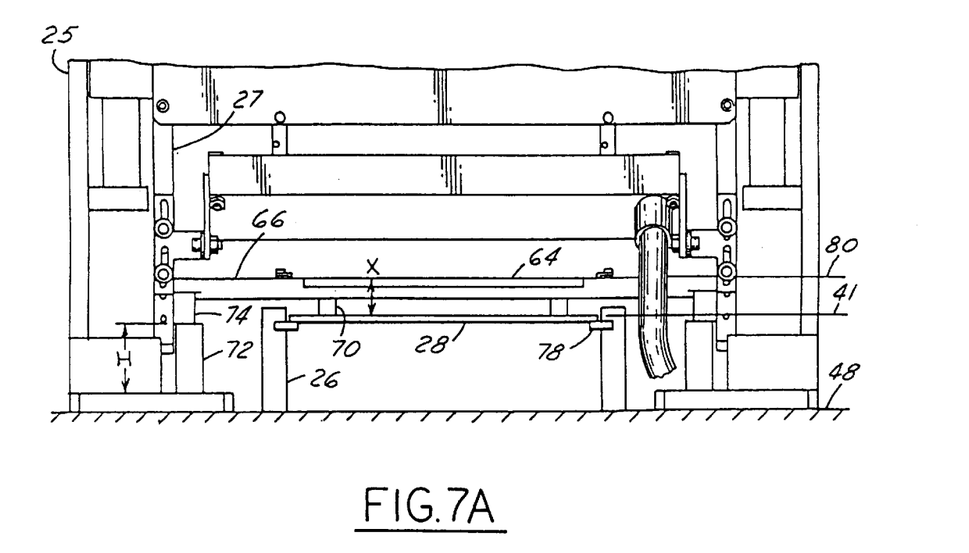
FIG. 7a is a partial front view of the multicamera staging structure showing the photo-tool fixture assembly, gauge block and gauge shim deployment utilized in the conveyor unit alignment process.
Figure 7B:
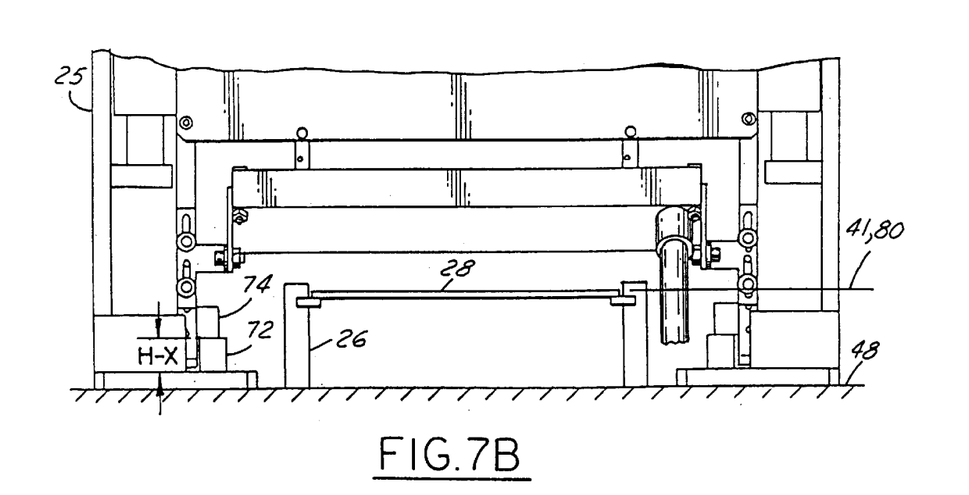
FIG. 7b is a partial front view of the multicamera staging structure showing the gauge block deployment utilized during the operation of the machine vision image data acquisition system.

Referring now to FIG. 7 which depicts the component configuration used in the conveyor unit alignment process, attached to the inside of each of the two inside vertical stage supports 27 are photo-tool fixture mounting blocks 74 which are doweled to receive a photo-tool fixture assembly 66 holding a precision photo-tool 64. By turning the adjusting knobs 68 (shown in FIG. 1) attached to the lead screws of the Stelron Slides 36, the multi-camera staging structure 24 and the photo-tool fixture assembly 66 move up and down as a rigid unit. Placed on the two base plates of the outside vertical frame supports 25 are gauge blocks 72 of height H and width H-X (width shown in FIG. 7b). The two belts 78 of the conveyor unit 26 support a printed circuit board 28. Two gauge shims 70 are deployed between the bottom of the photo-tool fixture 66 and the top of the printed circuit board 28 to establish parallelism between the calibration plane 80 and the top surface of the printed circuit board 28 which defines the pcb inspection plane 41.

Figure 8:
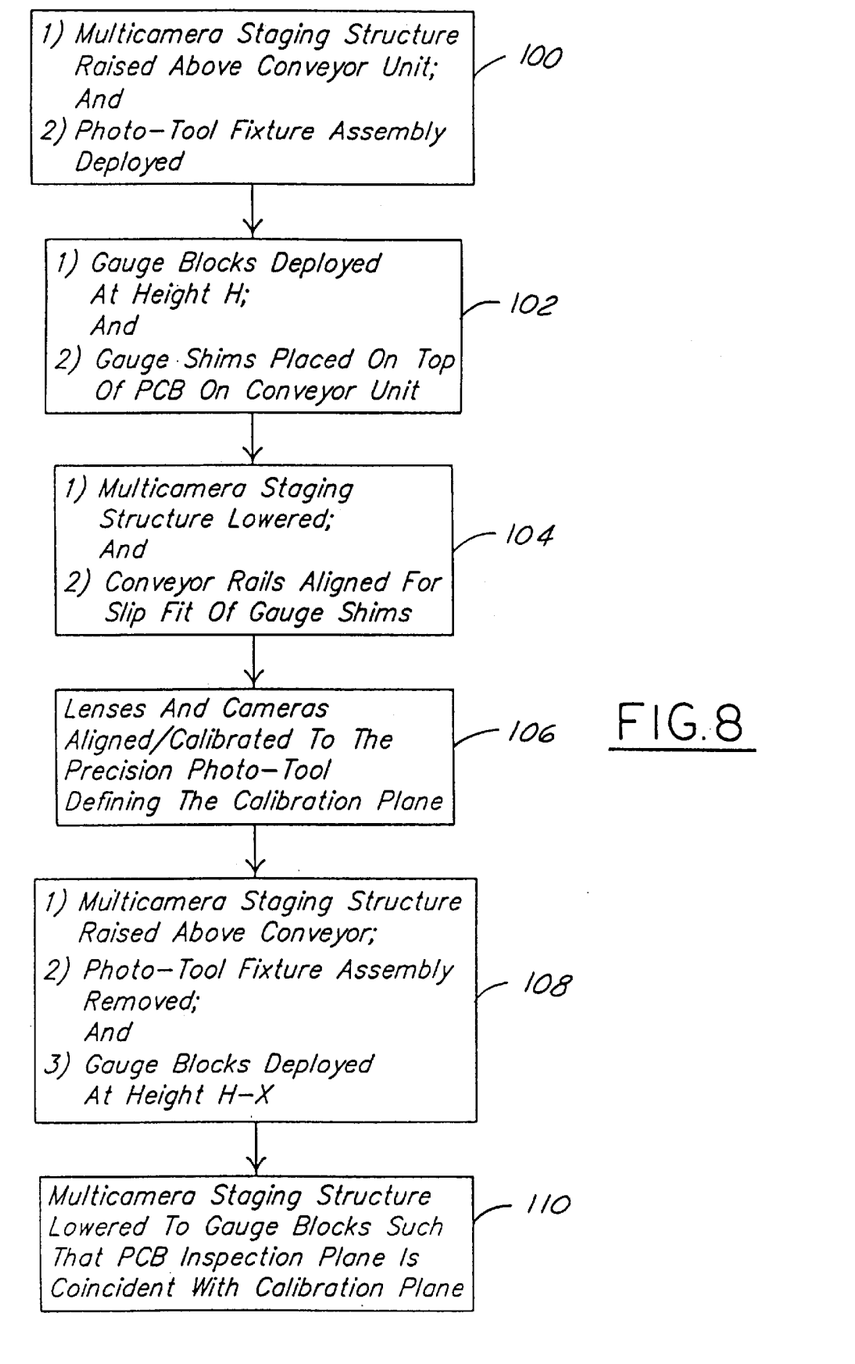
FIG. 8 is a flow chart outlining the conveyor unit alignment process including the camera and lens calibration step.

Referring now to FIG. 8, the conveyor and image inspection plane alignment process begins in step 100 as the technician raises the multi-camera staging structure 24 above the conveyor unit 26 using the adjusting knobs 68 and places the photo-tool fixture assembly 66 containing the precision photo-tool 64 onto the photo-tool fixture mounting blocks 74. In step 102, the two gauge blocks 72 are deployed at height H (as shown in FIG. 7a) on top of the base plates of the outside vertical frame supports 25. The gauge shims 70 are placed on the top at each edge of the printed circuit board 28. In step 104, the multicamera staging structure 24 is lowered until the photo-tool fixture mounting blocks 74 meet the gauge blocks 72. The conveyor unit 26 is adjusted such that a slip fit of the gauge shims 70 is created between the bottom of the photo-tool fixture assembly 66 and the top of the printed circuit board 28 setting up the critical dimension X as measured from the top surface of the precision photo-tool 64 to the bottom surface of the gauge shims 70 and establishing parallelism between the calibration plane 80 and the pcb inspection plane 41. In step 106, alignment and calibration of the lenses 23 and the L-bracket video cameras 22 to the calibration plane 80 is performed. In step 108, the multicamera staging structure 24 is again raised away from the conveyor unit 26. The photo-tool fixture assembly 66 is removed and the gauge blocks 72 are turned 90 degrees to a height of H-X. Finally in step 110, the multicamera staging structure 24 is again lowered until the photo-tool fixture mounting blocks 74 meet the gauge blocks 72 such that the calibration plane 80 and the pcb inspection plane 41 are now co-incident as shown in FIG. 7b.

The above-described multicamera staging structure 24 results in a machine vision image data acquisition system 20 that is more flexible than previously known single moving camera and fixed multiple camera systems. The sensor coverage of the machine vision image data acquisition system 20 can be varied to accommodate various sizes of printed circuit boards 28 by adding or subtracting L-bracket camera 22 and lens 23 assemblies. The multicamera staging structure 24 can also be configured for other inspection resolutions by replacing the mounting bars 42 and 44, the lens alignment plates 38 and 39, and the inside vertical staging supports 27 to accommodate camera lenses 23 with varying magnifications and cameras 22 of varying array sizes. In addition, the fixed multicamera staging structure 24 provides a rigid and stable platform that permits the precision mounting of the various components which allows for the use of lenses 23 and L-bracket video cameras 22 having high resolution and sensitivity.

Figure 3:
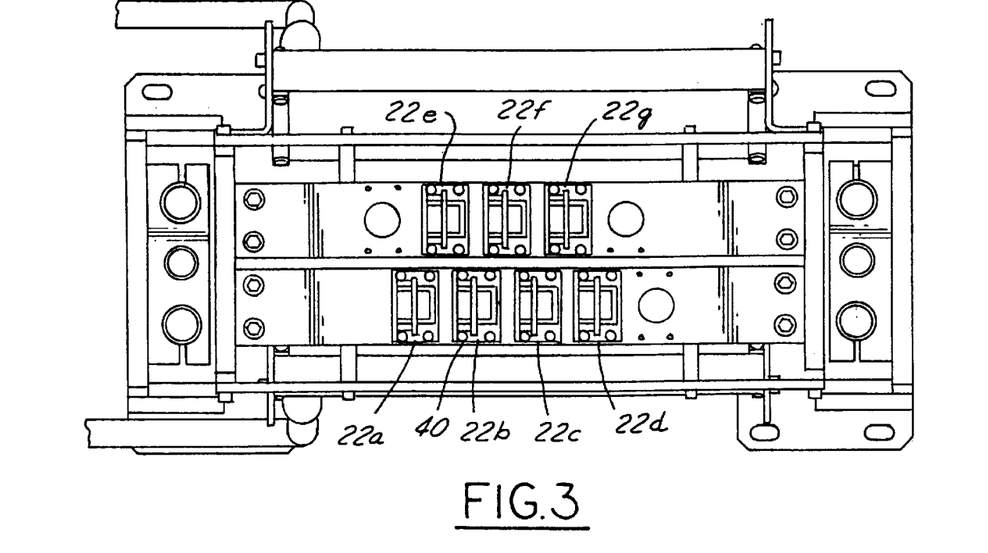
FIG. 3 is a top view in the direction of arrow 3 of FIG. 2 showing the multicamera staging structure.
Figure 5:
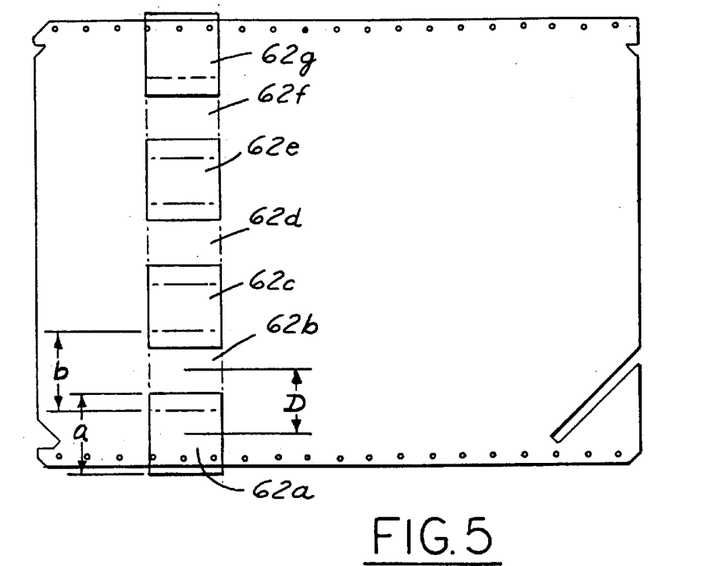
FIG. 5 is a plan view of a printed circuit board showing dual rows of registration fiducials and the combined two-dimensional inspection area of the cameras including their overlapping fields of view.

For example, the preferred embodiment of the described machine vision image-data acquisition system 20 shown in FIGS. 1 and 3 is configured with four lenses 23a, 23b, 23c and 22d and corresponding L-bracket video cameras 22a, 22b, 22c and 22d in the lower bank 37 and three such lenses 23e, 23f, and 23g and corresponding L-bracket video cameras 22e, 22f, and 22g in the upper bank 35. Thus, the preferred embodiment utilizes seven L-bracket video cameras 22 each having a 1 mil (i.e., 0.001 inch) pixel resolution and a 0.90 inch×0.67 inch field of view. The distance between the centerlines of adjacent L-bracket video camera 22 and lens pairs in the upper and lower banks 35 and 37, for example 22a and 22e, is 0.80 inches. This camera mounting centerline distance results in a two-dimensional horizontal inspection area or web of 5.70 inches×0.67 inch across the printed circuit board 28 comprised of the seven corresponding overlapping fields of view 62a through 62g for the seven L-bracket video cameras 22 with a 0.10 inch overlap zone between the fields of view of adjacent L-bracket video cameras 22, as shown in FIG. 5.

Figure 6:
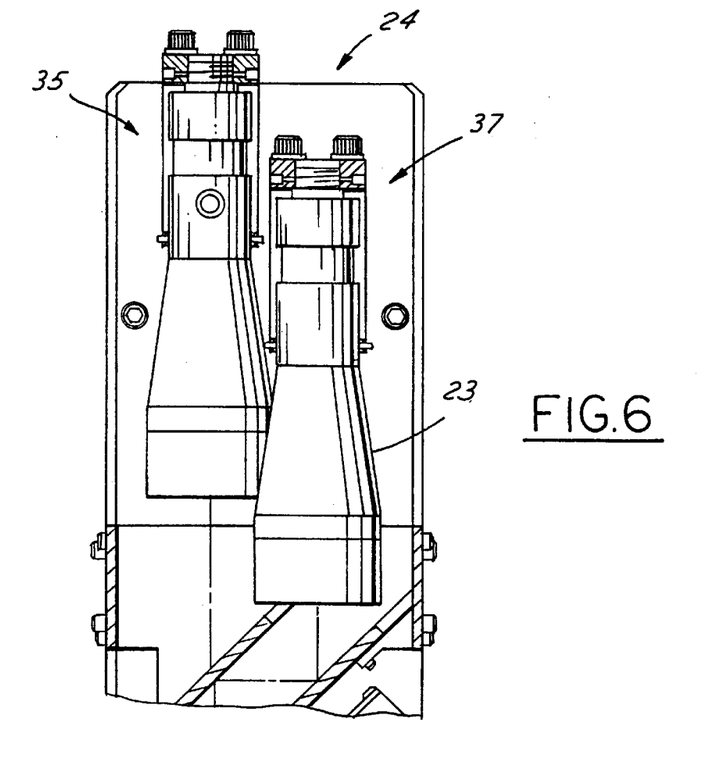
FIG. 6 is a vertical cross-sectional view taken along line 2—2 of FIG. 1 showing the multicamera staging structure configured with 2 mil resolution lenses.

An alternative 2 mil resolution system is shown in FIG. 6 utilizing L-bracket video cameras 22 each having a 1.60 inch×1.20 inch field of view and 2.62 inch diameter lens 23. The 2 mil systems built by Chrysler Corporation are configured typically with four L-bracket video cameras 22, two video cameras 22 in the upper bank 35 and two video cameras 22 in the lower bank 37, with a camera mounting centerline distance of 1.5 inches. This configuration results in a two-dimensional horizonal inspection web of 6.10 inches×1.20 inches with 0.10 inch overlap zones. The lenses 23 used in this alternative configuration have a telecentricity of less than 1%, distortion of less than 1%, magnification of 0.2133x±5% with an object distance of 7.51 inches nominally.

It may be apparent to one skilled in the art that if the beam splitter/mirror assembly 55 was oriented at angle other than 45 degrees to the pcb inspection plane 41, the orientation of the L-bracket video cameras 22 and lenses 23 could be modified to achieve the advantages of the present invention. Other modifications and alternative constructions will, of course, be apparent to those skilled in the art who should realize that such variations made to the disclosed embodiments may still properly fall within the scope of the present invention as defined by the claims which follow.

What I claim is:

1. An image data acquisition system for acquiring visible spectrum image data for use in the inspection of a circuit board transported on a conveyor, comprising:

a structure substantially rigid against lateral motion located adjacent to said conveyor, said structure including a first outside member and a second outside member being spaced apart, a first slide unit and a second slide unit, and a rigid inside structure, said inside structure including a first lateral surface and a second lateral surface positioned substantially parallel to and between the first and second outside members, said inside structure further including a first horizontal camera mounting surface located at a first level above the conveyor and a second horizontal camera mounting surface located at a second level above the conveyor and first and second alignment plates, where the first level is farther from the conveyor than the second level, both of the first and second mounting surfaces and the first and second alignment plates being attached to both of the first and second lateral surfaces, wherein the first slide unit is attached to the first lateral surface and the first outside member and the second slide unit is attached to the second lateral surface and the second outside member such that the inside structure is slidable on the first and second slide units to be movable relative to the first and second outside members; and a plurality of first cameras defining a first camera bank mounted on said first camera mounting surface and attached to the first alignment plate and a plurality of second cameras defining a second camera bank mounted on the second camera mounting surface and attached to the second alignment plate to sense at least a partially contiguous field of view on said circuit board.

2. The image data acquisition system of claim 1, further comprising:

a plurality of lenses, one of said lenses mounted in an axial pair with each of said cameras such that said camera and lens axes are oriented at a substantially right angle to said circuit board.

3. The circuit board inspection system of claim 2, each said video camera further comprising:

a sensor array, mounted to said structure, for receiving light passing through at least one of said lenses and outputting a signal based upon said received light;

a sampling and signaling conditioning processing unit in communication with said sensor array for obtaining data from said sensor array; and a camera data-image processing unit, in communication with said sampling and signal conditioning unit, for processing data received from said sampling and signaling conditioning processing unit.

4. The image data acquisition system of claim 2, wherein said camera lenses have a telecentricity of less than 2 degrees.

5. The image data acquisition system of claim 1, further comprising:

a mirror mounted to said structure such that light striking said mirror is reflected into each of the cameras in said second bank; and a beam splitter mounted to said structure such that light striking said beam splitter is partially reflected toward said mirror and partially transmitted through the body of said beam splitter into each of the cameras in said first bank.

6. The image data acquisition system of claim 1, further comprising a light source mounted to said structure above said circuit board to deliver distributed light to said circuit board.

7. A visual inspection system for sensing characteristics of a circuit board transported on a conveyor, comprising:

at least two outside members spaced apart above said conveyor;

a slide unit attached to each outside member;

a rigid inside structure including a first lateral surface and a second lateral surface positioned substantially parallel to and between the first and second outside members, said inside structure further including a first horizontal mounting surface located at a first level above said conveyor and a second horizontal mounting surface located at a second level above said conveyor and first and second alignment plates, where the first and second levels are at different distances from the conveyor, both of the first and second mounting surfaces and the first and second alignment plates being attached to both of the first and second lateral surfaces, at least one slide unit attached to each lateral surface; and a plurality of optical sensors mounted on the first mounting surface and a plurality of optical sensors mounted on the second mounting surface to sense an image on said circuit board such that said inside structure is displaced relative to said outside members during calibration of at least one of said optical sensors.

8. The system of claim 7 further comprising:

a plurality of lenses, one of said lenses being mounted in line with each of said optical sensors such that the axis of each optical sensor and lens pair is oriented at a substantially right angle to said circuit board.

9. The system of claim 8, wherein each said optical sensor comprises:

light array means mounted to said inner structure for sensing light passing through each lens; and sampling and signal conditioning means for sampling the intensity of light reflected from said circuit board and conditioning said sampled signal; and processing means, in communication with said sampling and signal means, for receiving and digitizing said conditioned signal for transmission.

10. The system of claim 8, wherein said lenses are telecentric.

11. The system of claim 8, further comprising illumination means, mounted to said inside structure above said circuit board for delivery of distributed illumination to said circuit board.

12. The system of claim 7, further comprising:

reflecting means mounted to said inside structure such that light striking said reflecting means is reflected into said optical sensors located on said first level; and light splitting means mounted to said inside structure such that light striking said light splitting means is partially reflected toward said reflecting means and partially transmitted through said light splitting means into said optical sensors located on said second level.

13. An image data acquisition system for acquiring visible spectrum image data for use in the inspection of a circuit board transported on a conveyor, comprising:

a structure substantially rigid against lateral motion located adjacent to said conveyor, said structure including a first outside member and a second outside member being spaced apart, a first slide unit and a second slide unit, a first lateral surface and a second lateral surface, a first horizontal camera mounting surface and a second horizontal camera mounting surface located above the conveyor, and a first alignment plate and a second alignment plate, said first and second lateral surfaces positioned substantially parallel to between the first and second outside members, where the first mounting surface is farther from the conveyor than the second mounting surface, both of the first and second mounting surfaces and the first and second alignment plates being attached to both of the first and second lateral surfaces, wherein the first slide unit is attached to the first lateral surface and the first outside member and the second slide unit is attached to the second lateral surface and the second outside member such that the first and second camera mounting surfaces are movable relative to the first and second outside members;

a plurality of first cameras defining a first camera bank mounted on the first camera mounting surface and attached to the first alignment plate, and a plurality of second cameras defining a second camera bank mounted on the second camera mounting surface and attached to the second alignment plate to sense at least a partially contiguous field of view directionally on said circuit board;

a plurality of lenses, one of said lenses being mounted in an axial pair with each of said cameras such that said camera and lens axes are oriented at a substantially right angle to said circuit board;

a mirror mounted to said structure such that light striking said mirror is reflected into the cameras mounted on the second mounting surface; and a beam splitter mounted to said structure such that light striking said beam splitter is partially reflected toward said mirror and partially transmitted through the body of said beam splitter into the cameras mounted on the first mounting surface.

14. The image data acquisition system of claim 13, further comprising a light source mounted to said structure above said circuit board to deliver distributed light to said circuit board.

\* \* \* \* \*